US00PP13955P29

(12) United States Plant Patent
Sijm

(10) Patent No.: US PP13,955 P2
(45) Date of Patent: Jul. 8, 2003

(54) IMPATIENS PLANT NAMED 'HGI-1036-1'

(75) Inventor: Johannes J. G. Sijm, Andijk (NL)

(73) Assignee: Hem Genetics B.V., Hem (NL)

( * ) Notice: Subject to any disclaimer, the term of this patent is extended or adjusted under 35 U.S.C. 154(b) by 0 days.

(21) Appl. No.: 10/078,484

(22) Filed: Feb. 21, 2002

(51) Int. Cl.[7] ..... A01H 5/00

(52) U.S. Cl. ..... Plt./317

(58) Field of Search ..... Plt./317

*Primary Examiner*—Bruce R. Campell
*Assistant Examiner*—Anne Marie Grünberg
(74) *Attorney, Agent, or Firm*—Foley & Lardner

(57) ABSTRACT

A new and distinct Impatiens plant named 'HGI-1033-3' characterized by having a typical compact growth, small flowers and a clear white flower color.

2 Drawing Sheets

Latin name of the genus and species of the plant claimed: *Impatiens walleriana.*
Variety denomination: HGI-1036-1.

BACKGROUND OF THE INVENTION

The present invention relates to a new and distinct cultivar of Impatiens plant, botanically known as *Impatiens walleriana,* and hereinafter referred to by the cultivar name 'HGI-1036-1'.

The new cultivar originated from a cross made in a controlled breeding program in the village of Hem, the Netherlands. The female parent is 'IB-2-4' (unpatented). The male parent is 'IB-17-2' (unpatented). 'HGI-1036-1' was discovered and selected by the inventor Johannes J. G. Sijm, in November 1999, as a flowering plant within the progeny of the stated cross in a controlled environment in the village of Hem, the Netherlands.

'HGI-1036-1' is a product of a planned breeding program conducted by the inventor and selected in a controlled cultivated environment in the village of Hem, the Netherlands. Asexual reproduction of the new cultivar by vegetative cuttings used in propagation was first performed in December 1999 in the village of Hem, the Netherlands and has demonstrated that the combination of characteristics as herein disclosed for the new cultivar are firmly fixed and reproduce true to type in successive generations of asexual reproduction.

BRIEF DESCRIPTION OF THE INVENTION

The following traits have been repeatedly observed and are determined to be basic characteristics of 'HGI-1036-1' which in combination distinguish this Impatiens as a new and distinct cultivar:

1. Compact growth;
2. Small flowering;
3. Small leaves; and
4. Clear white flower color.

'HGI-1036-1' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in the village of Hem, the Netherlands under conditions which closely approximate those generally used in commercial practice.

Of the many commercial cultivars known to the present inventor, the most similar in comparison to 'HGI-1036-1' is the cultivar 'Firefly White'. The overall habit and appearance for 'HGI-1036-1' and 'Firefly White' are comparable, however 'HGI-1036-1' has a more compact growth, the flowers are slightly larger, and the flower color of 'Firefly White' is RHS 155A, whereas the flower color of the instant plant is RHS 155C.

In comparison to the instant plant, both parental cultivars have a more vigorous plant habit. When grown under the same conditions in a greenhouse as potted plants, the parental cultivars are 50% taller than 'HGI-1036-1'. The flower color of parental cultivars differ from 'HGI-1036-1'. Flowers of the female parental cultivar are RHS 155B; flowers of the male parental cultivar are RHS 43C, and are larger, 4–5 cm in diameter.

BRIEF DESCRIPTION OF THE DRAWING

The accompanying photographic illustrations show typical flower and foliage characteristics of 'HGI-1036-1' with colors being as true as possible with illustrations of this type.

The first drawing shows the plant in its entirety, with compact growth and numerous flowers.

The second drawing shows an enlargement of one typical flower.

DETAILED BOTANICAL DESCRIPTION

The following observations, measurements and values describe the new cultivar as grown in the village of Hem, the Netherlands, under conditions which closely approximate those generally used in commercial practice. The plant grows well under normal greenhouse conditions, however the temperature should not decrease below 15 degrees Centigrade. Shading of the plants in high light conditions is essential. Color references are made to The Royal Horticultural Society Colour Chart (R.H.S.), except where general colors of ordinary significance are used. Color values were taken under daylight conditions at approximately noon in the village of Hem, the Netherlands.

Parentage:

*Female parent.*—IB-2-4.

*Male parent.*—IB-17-2.

Propagation:

*Type cutting.*—Stem cutting.

Plant: General Appearance and Form:

*Height.*—Average 9 centimeters, depending on cultivation conditions and when growing in a pot of 10 centimeters wide.

*Width.*—Average 10 centimeters, depending on cultivation conditions.

*Growth and branching habit.*—Upright and freely branching.

*Flowering response.*—Day length neutral.

*Flowering season.*—Year-round in controlled climate conditions; outdoors until start of frost period.

*Winter hardiness.*—No.

*Lastingness of the individual bloom.*—5 to 7 days depending on temperature of the environment.

*Crop time.*—6 weeks from cutting to plant.

*Time to initiate roots.*—10 to 12 days at an average of 22 degrees Centigrade.

*Time to develop roots.*—18 to 21 days at an average of 21 degrees Centigrade.

*Rooting habit.*—Fibrous, branching and fine roots.

*Fragrance.*—None.

Foliage:

*Overall shape of leaf.*—Lanceolate to elliptic. Base: Acute. Tip: Acute.

*Margin.*—Crenate with ciliation.

*Texture.*—Soft.

*Main color of upper surface.*—Mature leaf: RHS 137B. Immature leaf: RHS 137B.

*Main color of lower surface.*—Mature leaf: RHS 138B. Immature leaf: RHS 138B.

*Venation color.*—Upper surface: Pinnate RHS 137B. Lower surface: RHS 138B.

*Size.*—Length: 4 centimeters. Width: 2.5 centimeters.

*Leaf base shape.*—Acute.

*Leaf apex shape.*—Acute.

*Petiole.*—Length: 2 centimeters. Diameter: 0.2 centimeters. Color: RHS 146D.

Flower description:

*Flower type and habit.*—Single, placed in upper leaf axils.

*Flowering season.*—Year-round in controlled climate conditions; outdoors until start of frost period. Flower size: 2.5 cm long; 2.2 cm wide. Average Number: 2 to 7 per leaf axil, large numbers per plant. Height: 3 centimeters. Petals: Number/Arrangement: 5, arranged around the stamen. Length: 1.3 centimeters. Width: 0.9 centimeters. Shape: Upper petal round shaped, the remaining oval shaped. Base: Acute. Margin: Sharp. Texture: Soft. Color: Upper surface: RHS 155C. Lower surface: RHS 155C.

*Stem.*—Average length: 1.5 centimeters depending on cultivation conditions. Average diameter: 15 millimeters. Color: RHS 138B.

*Spur.*—Color: RHS 155C. Length: 2 cm.

*Bud.*—Response: Day length neutral. Color: RHS 155C. Size before opening: 0.5 centimeter. Pedicel Length: Starting at 0 cm and stretching to 2 centimeters. Pedicel Color: RHS 138A.

*Reproductive organs.*—Stamen: 1, color RHS 141B. Seed/Fruit Development: None. Anthers: Caps over pistil, drops off when flower matures. Color: RHS 155B. Pollen: None. Stigma: Star-shaped when opened, color RHS 155 B. Ovary: Color RHS 141 B.

*Pest/disease resistance/susceptibility.*—No observations to date.

I claim:

1. A new and distinct Impatiens plant named 'HGI-1036-1' substantially as illustrated and described herein.

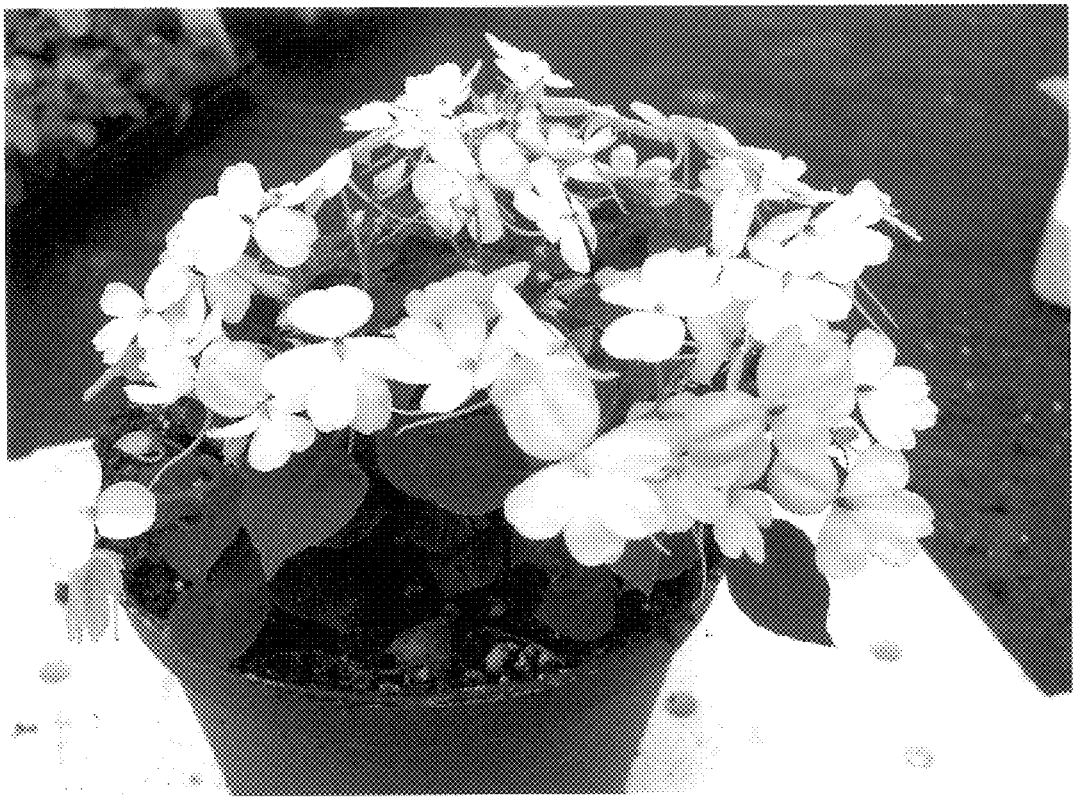

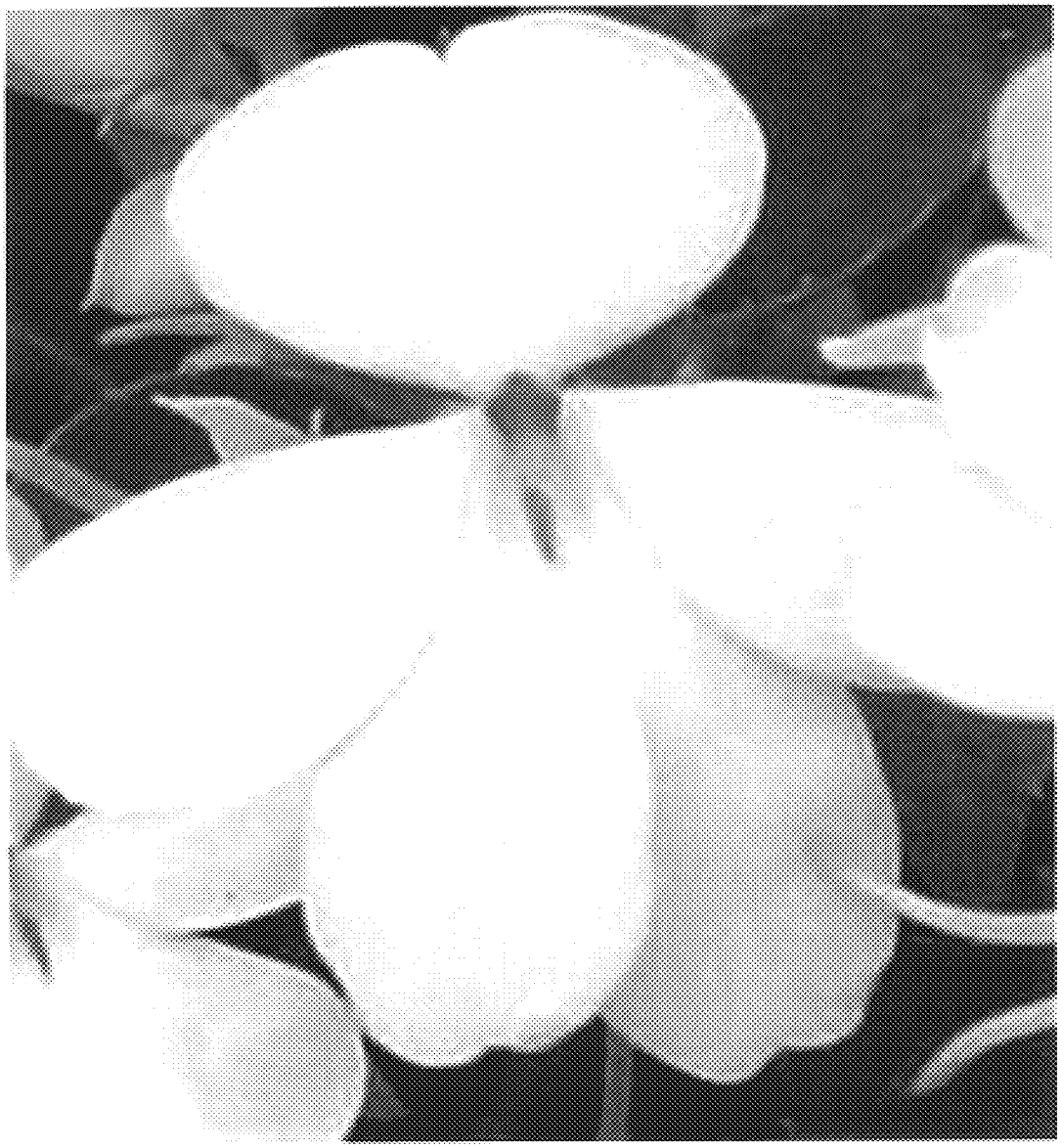

* * * * *